United States Patent

Huang et al.

[11] Patent Number: 5,907,099
[45] Date of Patent: May 25, 1999

[54] ULTRASONIC DEVICE WITH ENHANCED ACOUSTIC PROPERTIES FOR MEASURING A VOLUME AMOUNT OF FLUID

[75] Inventors: Bao Tuan Huang, Antony; Gabriel Marquette, Villiers Saint Frédéric, both of France

[73] Assignee: Schlumberger Industries, S.A., Montrouge, France

[21] Appl. No.: 08/809,159

[22] PCT Filed: Aug. 4, 1995

[86] PCT No.: PCT/FR95/01051

§ 371 Date: Aug. 27, 1997

§ 102(e) Date: Aug. 27, 1997

[87] PCT Pub. No.: WO96/06333

PCT Pub. Date: Feb. 29, 1996

[30] Foreign Application Priority Data

Aug. 23, 1994 [FR]   France ................................... 94 10199

[51] Int. Cl.⁶ ....................................................... G01F 1/66
[52] U.S. Cl. ........................ 73/597; 73/861.27; 73/861.31
[58] Field of Search ........................... 73/861.28, 861.29, 73/861.31, 861.27, 597

[56] References Cited

U.S. PATENT DOCUMENTS

| 4,480,486 | 11/1984 | Meisser et al. ........................ 73/861.28 |
| 4,506,552 | 3/1985 | Brown et al. ......................... 73/861.28 |
| 5,243,863 | 9/1993 | Gill ....................................... 73/861.28 |
| 5,383,369 | 1/1995 | Khuri-Yakub et al. .............. 73/861.29 |

FOREIGN PATENT DOCUMENTS

| 48791 | 4/1982 | European Pat. Off. ............ 73/861.28 |
| WO94/17372 | 8/1994 | WIPO ................................. 73/861.28 |
| WO94/20821 | 9/1994 | WIPO ................................. 73/861.28 |

*Primary Examiner*—Hezron Williams
*Assistant Examiner*—Nashmiya Fayyaz
*Attorney, Agent, or Firm*—Leonard W. Pojunas

[57] ABSTRACT

An ultrasonic measurement device measures a volume-related quantity of a fluid flowing from a first zone to a second zone of the device. The device includes two ultrasound transducers emitting and receiving ultrasound signals and each disposed in one of the zones to define between them an ultrasound measurement path in the fluid. The device also includes a measurement electronics block that drives emission and reception of ultrasound signals by transducers, measures a physical magnitude characteristic of the propagation speed of said signals in the fluid and deduces the volume-related quantity of the fluid from these measurements and the geometry of the device. This determines the volume-related quantity of the fluid on the basis of measurements of a physical magnitude that is characteristic of the propagation speed of ultrasound signals in the fluid. The device also includes firstly, over at least a portion of the ultrasound measurement path, two concentric ducts about the longitudinal axis (XX') defining a longitudinal space, and secondly the inner duct being obstructed by a central element subdividing the inside of said inner duct into two internal housings enabling ultrasound measurement to be performed solely in the longitudinal space.

19 Claims, 6 Drawing Sheets

ULTRASONIC DEVICE WITH ENHANCED ACOUSTIC PROPERTIES FOR MEASURING A VOLUME AMOUNT OF FLUID

BACKGROUND OF THE INVENTION

The invention relates to a device for ultrasound measurement of a volume-related quantity of a fluid, which device makes it possible to limit the number of acoustic propagation modes, and to improve the linearity of its calibration curve.

It is widely known to use ultrasound transducers for measuring a volume-related quantity of a fluid flowing along a duct. Conventionally, the ultrasound transducers are spaced apart from each other in the fluid flow, defining between them an ultrasound measurement path, and they are disposed, for example, face to face and in alignment on the longitudinal flow direction, or else they are mounted in one of the walls of the duct.

Alternatively, the transducers emit and receive ultrasound signals propagating in the fluid flow and electronic means are provided for determining the volume-related quantity of fluid flowing along the duct on the basis of measurements of at least one physical magnitude that is characteristic of the propagation speed of ultrasound signals in the fluid flow. By way of example, one such physical magnitude is the propagation time of ultrasound signals, and another is the phase thereof.

It is also known that devices implementing this type of measurement are subject to measurement errors that show up as lack of accuracy in the measurement and as non-linearity of the calibration curve for such a device. These errors are largely attributable to ultrasound waves propagating in the fluid flow in numerous acoustic modes other than plane mode, thereby giving rise to interfering phase shifts.

International patent application WO 93/00570 proposes a method of reducing such errors based on a technique of transmitting wave packets, in which every four wave packets are inverted relative to the preceding packets so as to cancel the effects of higher propagation modes in the duct. Although that method is effective, it nevertheless suffers from the drawback of being complicated to manage from the points of view of the associated electronics and of signal processing, and it consumes a non-negligible amount of energy.

International patent application WO 94/09342 describes an ultrasound measurement device in which the two ultrasound transducers are spaced apart in the fluid flow direction from the inlet to the outlet of the device, and including means for measuring the propagation times of ultrasound signals between the two transducers. That device defines a plurality of fluid flow passages that are mutually parallel, with each passage being dimensioned so as to have a characteristic cutoff frequency for wave propagation in plane mode that is higher than the transmission frequency of the ultrasound, thereby ensuring that waves can propagate in plane mode only along said passage. Such a device does not consume additional energy but it does introduce further interfering phase shifts due to the presence of the plurality of passages, and the interfering phase shifts affect the linearity of the calibration curve.

SUMMARY OF THE INVENTION

The present invention seeks to remedy the drawbacks of the prior art by proposing a device for ultrasound measurement of a volume-related quantity of a fluid, which device is simple, requiring no additional signal processing other than that required for ultrasound measurement, and giving rise to no interfering phase shifts liable to produce measurement errors that are unacceptable in the intended applications, such as gas metering.

The present invention thus provides an ultrasound measurement device for measuring a volume-related quantity of a fluid flowing from a first zone to a second zone of said device, the device including at least two ultrasound transducers suitable for emitting and for receiving ultrasound signals, each being disposed in one of said zones of the device and defining between them an ultrasound measurement path in the fluid, the device also having means for determining the volume-related quantity of said fluid from measurements of at least one physical magnitude characteristic of the propagation speed of the ultrasound signals in the fluid, the ultrasound measurement device being characterized in that it further includes firstly, on at least a portion of the ultrasound measurement path, two concentric ducts about a longitudinal axis, comprising an outer duct and an inner duct defining a longitudinal space between their respective inner and outer surfaces, and secondly, means enabling ultrasound measurement to be performed solely in the longitudinal space.

This characteristic makes it possible in simple manner to restrict the number of propagation modes and to reduce interfering phase shifts considerably.

Advantageously, the inner duct is obstructed by a central element subdividing the inside of said inner duct into two internal housings, thereby constraining the fluid to pass from the first zone towards the second zone via the longitudinal space.

Thus, while ultrasound signals are being emitted by one of the ultrasound transducers, the major portion of the signals propagates in the longitudinal space providing the transducers are selected appropriately, while a small portion of said emitted signals, referred to as "interfering" signals, propagates in the portion of the internal housing that is situated at the same end as the emitter.

This small portion of ultrasound signals propagating in the internal housing encounters the central element and is reflected thereon, so as to propagate inside the internal housing back towards the emitter. When said small portion of ultrasound signals reaches the emitter again, the major portion of the ultrasound signals that has passed via the longitudinal space has already been received by the other transducer so it now matters little that the emitter is receiving reflected signals.

It is possible to provide for the central element to present a surface facing each internal housing that is either concave or convex so as to constrain the ultrasound signals propagating in the internal housing to reflect on the inside walls of said internal housing, thereby increasing their transit time and thus delaying the arrival of reflected interfering signals at the emitter. This makes it possible to lengthen the emission and/or reception of the ultrasound signals without the emitted signals being disturbed.

It is also possible to attenuate the propagation of the ultrasound signals in the internal housing of the inner duct by providing a lining of ultrasound-absorbent material on at least a fraction of the length of said internal housing. In this way, the ultrasound signals propagating along the internal housing are, so to speak, trapped in the housing so emission of ultrasound signals by the emitting transducer can be extended without fear of being disturbed by reflected interfering signals.

According to an advantageous characteristic of the invention, the central element subdividing the inside of the inner duct into two internal housings is, for example, a partition that is secured to the inner duct. It is thus possible to use a single part for manufacturing simply and simultaneously both the central element and the inner duct with its two internal housings.

In addition, given that the distance between each ultrasound transducer and the partition secured to the inner duct is known, it is possible, between pairs of ultrasound measurements to use a single transducer to measure sound propagation speed, thereby making it possible to take account of variations in the properties of the fluid and thus to correct subsequent ultrasound measurements. For this purpose, the ultrasound transducers must be heavily damped in order to be able to switch from acting as an emitter to acting as a receiver before the arrival of the first echo.

According to a further advantageous characteristic of the invention, the central element is, for example, a filler element made of an ultrasound-absorbent material. It is thus possible to attenuate the reflection of ultrasound signals directly in the internal housings of the inner duct without it being necessary to provide the inside surface of each housing with a lining of ultrasound-absorbent material.

The filler element may also have a surface that is concave or convex in shape looking into each of the internal housings in order to obtain interfering signals that are constrained to reflect on the walls of said internal housing, thereby increasing the propagation time of the ultrasound signals while simultaneously attenuating them.

In addition, when the longitudinal length of the inner duct is longer than that of the outer duct, and when the inner duct is located symmetrically relative to the outer duct, then the fluid flow leaving the longitudinal space gives rise to reduced recirculation and thus to smaller disturbance, thereby very considerably improving the quality of measurements over the entire range of flow rates.

The ultrasound transducers are preferably in alignment on the longitudinal direction of the longitudinal axis XX' so as to face the ends of the concentric ducts. It is also possible to envisage placing the transducers on the same wall of the device by tilting them towards each other so as to form a V-shaped ultrasound path and to dispose the ducts parallel to said wall on the V-shaped path.

According to a characteristic of the invention, when the transducers are in alignment with the longitudinal direction on axis XX', the distance e between each transducer and the corresponding longitudinal end of the inner duct lies in the range 0.1 l to 0.9 l where l is the distance between each transducer and the corresponding longitudinal end of the outer duct, and the distance l lies in the range 0.3 D to 3 D, where D is the inside diameter of the outer duct.

According to another characteristics of the invention, the longitudinal space has a flow cross-section whose largest radial dimension imparts a cutoff frequency characteristic of (0,2) propagation mode to said flow cross-section that is greater than the frequency of the ultrasound signals emitted by the transducers.

Quite unexpectedly, the Applicant has observed that this characteristic makes it possible to obtain measurements that are very accurate, with a calibration curve of improved linearity and that varies little as a function of the properties of the fluid (e.g. with different types of gas).

According to another characteristic of the invention, it may also be advantageous for the flow cross-section of the longitudinal space to have a larger radial dimension giving said section a cutoff frequency characteristic of (0,1) propagation mode which is higher than the frequency of the ultrasound signals emitted by the transducers, thus making it possible for plane mode only to propagate in the longitudinal space.

Advantageously, if the inner duct is not obstructed, it is possible to envisage using ultrasound transducers in which the sensitive portion is of a shape that matches the flow cross-section of the longitudinal space. For example, piezoelectric type transducers made of polymer (PVDF) are quite suitable, as are transducers of the type described in French patent application No. 94/07488.

Thus, by aligning such ultrasound transducers on the longitudinal direction of the longitudinal axis and by placing them close enough to the ends of the inner duct, e.g. at a distance e equal to 0.1 l, it is possible to transmit a major portion of the ultrasound energy only into the longitudinal space in which measurements are performed by an appropriate distribution of the sensitive portions of the transducers facing said longitudinal space, thereby avoiding interfering signals reflected in the inner duct and reflected back towards the ultrasound transducers. Consequently, in this configuration, the fluid also travels along the longitudinal passage situated inside the inner duct when passing from the first zone to the second zone, thereby making it possible to achieve lower head loss than is possible in the presence of an inner duct that is obstructed.

It is also quite possible to reduce the distance e between the transducers and the ends of the inner duct so that the fluid flows in the longitudinal space only.

Depending on the intended application, the flow cross-section of the longitudinal space can be dimensioned in such a manner as to give it a cutoff frequency characteristic of the (0,2) or (0,1) propagation mode which is higher than the frequency of the ultrasound signals emitted by the transducers.

In a first embodiment of the invention, the concentric ducts are tubes, thus conferring a flow cross-section to the longitudinal space which is annular in shape.

In a variant embodiment of the concentric ducts, the outer duct is a tube and the inner duct has a cross-section that is elliptical in shape.

In another variant embodiment of the concentric ducts, the outer duct is a tube and the inner duct has a cross-section that is square in shape.

In yet another variant embodiment of the concentric ducts, both concentric ducts have a transverse cross-section that is elliptical in shape.

Other characteristics and advantages appear from the following description given by way of non-limiting and illustrative example, and made with reference to the accompanying drawings, in which:

An ultrasound measurement device for measuring a volume-related quantity of a gas such as its flow rate is shown in FIGS. 1 to 4.

DETAILED DESCRIPTION OF FIGURES

Figure 1:
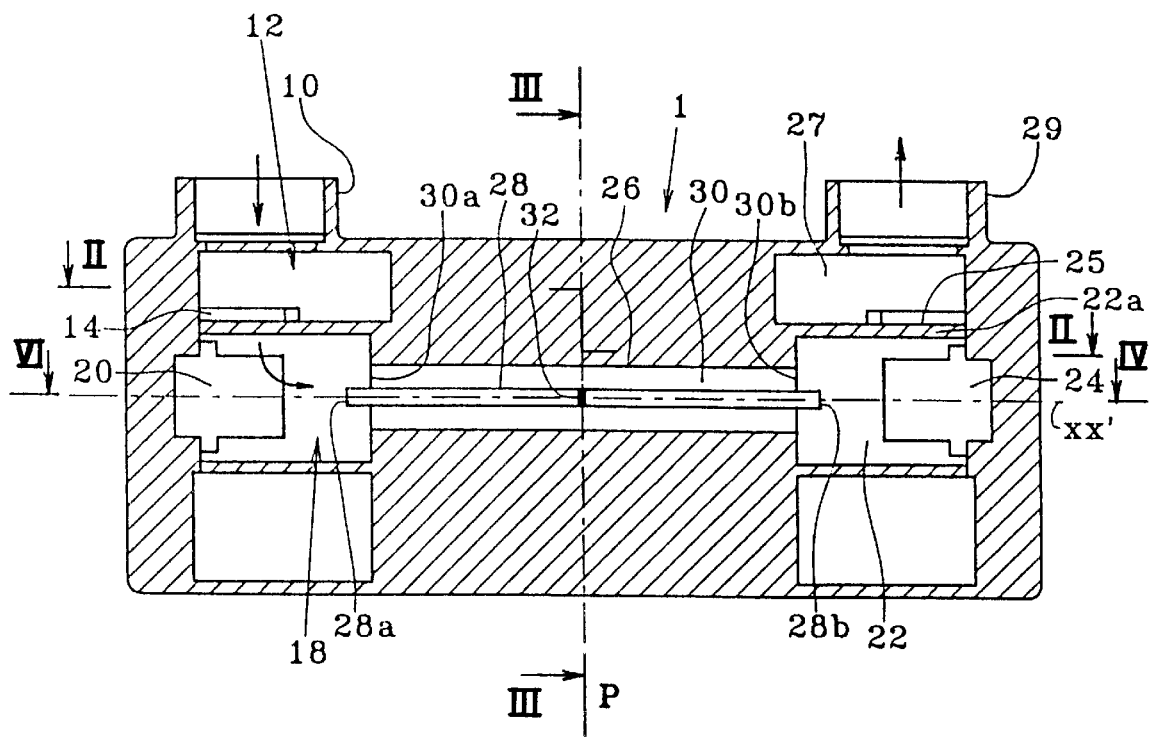
FIG. 1 is a diagrammatic longitudinal section of an ultrasound measurement device constituting a first embodiment of the invention.
Figure 2:
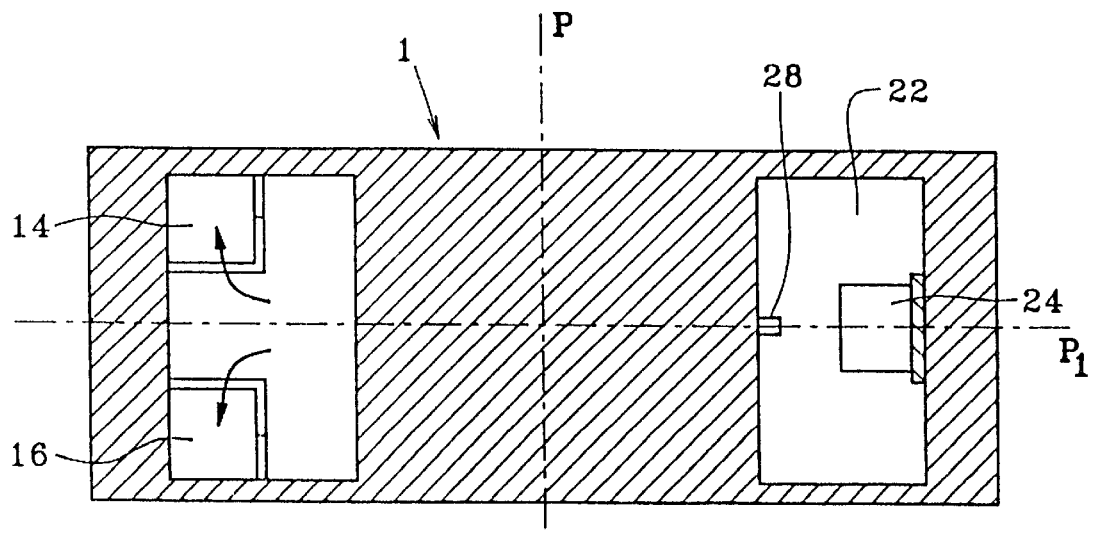
FIG. 2 is a diagrammatic longitudinal section on AA, showing the ultrasound measurement device of FIG. 1.

As shown in FIG. 1, the measurement device 1 constituting a first embodiment of the invention comprises a gas inlet 10 which opens out into a chamber 12 that is large in section compared with the section of said gas inlet. The chamber 12 has two lateral openings 14 and 16 (FIG. 2) which open out into a common chamber referred to as the "measurement" chamber 18 that is situated beneath the chamber 12 and in which an ultrasound transducer 20 is located. The measurement chamber 18 corresponds to a first zone of the device.

The measurement device 1 also includes another measurement chamber 22 in which another ultrasound transducer 24 is received and which corresponds to a second zone of the device, the gas flowing from the first zone towards the second zone. The two transducers 20 and 24 are thus disposed facing each other and in alignment on a longitudinal direction on axis XX' which corresponds to the longitudinal direction of gas flow between said transducers.

The transducers face each other, and between them they define an ultrasound measurement path in the gas, as described in greater detail below. The measurement chamber 22 has two lateral openings 23 and 25 formed in its top wall 22a (only one of the lateral openings, 25, is shown in FIG. 1). The two lateral openings 23 and 25 open out into a chamber 27 that is symmetrical to the chamber 12 about a plane P, said chamber 27 being connected to a gas outlet 29.

Thus, the flow of gas enters the measurement device 1 via its inlet 10 travelling in the direction of the arrow (FIG. 1), is subjected to considerable variation in pressure in the chamber 12, thereby greatly reducing its speed, and then splits into two symmetrical fractions about a plane $P_1$ (FIG. 2), each of the fractions travelling via a respective one of the lateral openings 14 and 16, thereby penetrating into the measurement chamber 18 on either side of the transducer 20 (FIG. 1). At this point the flow fractions re-unite to form a single flow along the above-mentioned ultrasound measurement path between the two transducers 20 and 24. Thereafter the gas flow opens out into the measurement chamber 22 and escapes therefrom by splitting again into two equal fractions each travelling via a respective one of the lateral openings 23 and 25 and then reforming a single flow inside the chamber 27 prior to leaving via the gas outlet 29.

Each transducer acts alternately as an emitter and as a receiver, and is connected to a measurement electronics block that is not shown in the figures. Conventionally, the measurement electronics block causes ultrasound signals to be emitted from one of the transducers 20 with said signals being received by the other transducer 24, and measures a physical magnitude characteristic of the propagation speed of said signals in the gas flow, e.g. its propagation time $t_1$. Conversely, the measurement electronics block also causes ultrasound signals to be emitted by the transducer 24, with said signals being received by the transducer 20, and it measures the corresponding propagation time $t_2$. Given the two measurements $t_1$ and $t_2$, and the dimensions of the flow section S of the gas between the two transducers, together with the distance L between the transducers, the measurement electronics block deduces the gas flow rate as follows:

$$Q = \frac{1}{2}LS \times \frac{t_2 - t_1}{t_2 \times t_2}$$

As described in European patent No. 0 347 096, it is also possible to measure propagation time and then to measure the phase shift induced by the propagation of the ultrasound signal, in order to refine the flow rate measurement.

The ultrasound measurement path between the two transducers is now described in detail. According to the invention, the measurement device includes two concentric ducts about the axis XX' and extending along at least a portion of the ultrasound measurement path, one of the ducts being referred to as the "outer" duct 26 and the other as the "inner" duct 28. Between them, i.e. between the inside surface of the outer duct 26 and the outside surface of the inner duct 28, the two ducts define a longitudinal space 30 along which gas can flow from the first zone 18 to the second zone 22.

Figure 4:
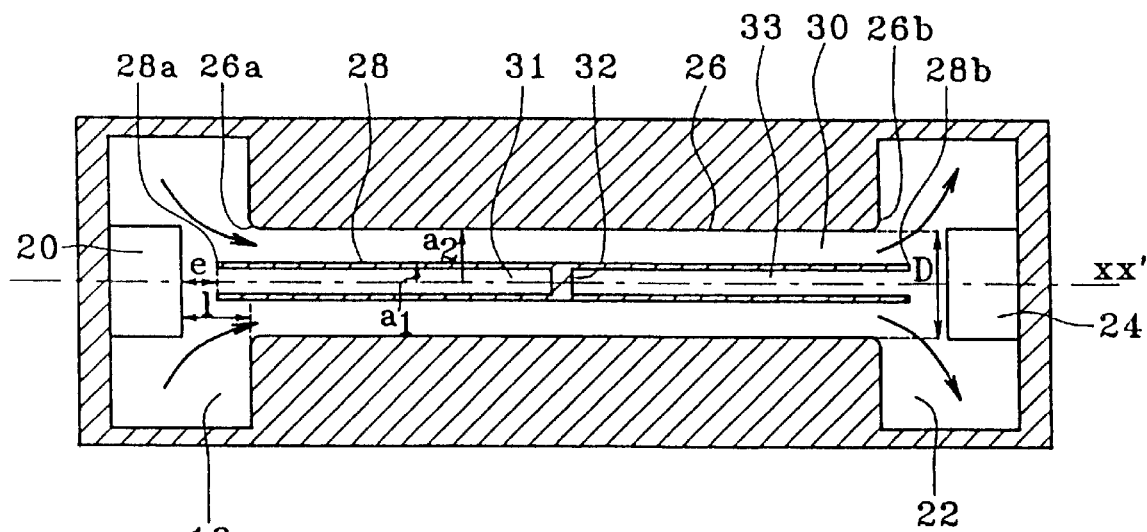
FIG. 4 is a fragmentary longitudinal section on CC showing the ultrasound measurement device of FIG. 1.

The device of the invention includes means for ensuring that gas flows from the first zone 18 to the second zone 22 and that ultrasound measurement takes place only in the longitudinal space 30. Advantageously, these means are formed by a central element that obstructs the central portion of the inner duct 28, thereby subdividing the inside thereof into two internal housings 31 and 33. As shown in FIGS. 1 and 4, this central element is a partition 32 secured to the inner duct 28 and formed when the two internal housings 31 and 33 are formed. This configuration makes it possible firstly for the ultrasound signals emitted by one of the transducers 20 and 24 and not travelling along the longitudinal space 30 to propagate in the internal housing that faces the emitting transducer, thereby avoiding any immediate interfering reflection, as would otherwise occur with an obstacle placed between the two ultrasound transducers.

Thus, this portion of the ultrasound signals is reflected on the central element and returns towards the emitting transducer, and reaches it when the signals travelling in the longitudinal space are received by the other transducer. Under such circumstances, signal emission is stopped, but it continues to be possible to receive ultrasound signals for the length of time that corresponds to the propagation time required by ultrasound to travel along the longitudinal space 30.

Figure 3:
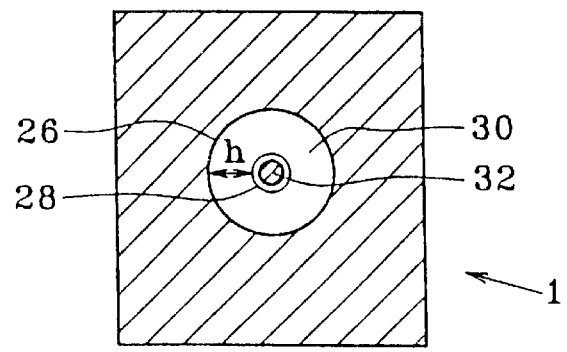
FIG. 3 is a diagrammatic cross-section on BB showing the ultrasound measurement device of FIGS. 1 and 2.

In the first embodiment of the invention as shown in FIGS. 1 and 4, the outer duct 26 is constituted by the walls of the measurement device that also serve to define the measurement chambers 18 and 22 so said outer duct does not penetrate into said measurement chambers. The inner duct 28 is fixed to the outer duct 26 by means of a support situated in the central portion of both ducts. This support is not shown in the figures and is constituted, for example, by two diametrically opposite radial ribs situated in the longitudinal space 30 and of sufficient size to hold the inner duct 28 rigidly inside the outer duct 26 without excessively disturbing the flow of gas or the propagation of ultrasound. The concentric ducts 26 and 28 may be tubes of constant diameter, for example, so that said longitudinal space has a constant flow cross-section that is annular in shape (FIG. 3). It is also possible to envisage the flow cross-section being not necessarily constant along the entire length of the ducts.

The configuration of the ultrasound measurement device 1 of the invention limits the number of propagation modes and considerably reduces interfering phase shifts relative to a structure constituted by a plurality of mutually parallel tubes as defined in international patent application WO 94/09342. Good measurements are thus obtained over the entire range of flow rates. In addition, the Applicant has observed an improvement in results by using an inner duct 28 that is longer than the outer duct 26 and that is disposed symmetrically relative to said outer duct. The gas is better channeled into the longitudinal space 30 at the inlet end 30a of said longitudinal space and the recirculation phenomenon that would otherwise occur at the outlet end 30b of said longitudinal space with both ducts having the same length is thus caused to be nonexistent.

For a given fluid, by an appropriate choice of the spacing between each of the transducers 20 and 24 and the inner and outer ducts 28 and 26, it is possible to reduce the fraction of the ultrasound signals travelling along the internal housing facing the transducer that is emitting. Thus, if the distance between the transducer 20 (or 24) and the facing end 28a (or 28b) of the inner duct 28 facing said transducer is written e (FIG. 4), and if the distance between the transducer 20 (or 24) and the end 26a (or 26b) of the outer duct 26 facing said transducer is written l and if the inside diameter of the outer duct 26 is written D, then the distances e and l should satisfy the following relationships:

$$0.1 \leq e \leq 0.9 \, l$$

$$0.3 \, D \leq l \leq 3 \, D$$

for the purposes firstly of transmitting a sufficient quantity of ultrasound energy via the longitudinal space 30, and secondly of avoiding the phenomenon of gas recirculation that would otherwise give rise to an interfering phase shift in the ultrasound measurements.

For axisymmetrical type ultrasound transducers, the distance e may be equal, for example, to ½ l and the distance l may be equal to 0.9 D.

In certain applications, depending on the desired measurement accuracy, it is possible to ensure that the greatest radial dimension h (FIG. 3) of the flow cross-section in the longitudinal space 30 gives said section a cutoff frequency $f_{02}$ characteristic of the (0,2) propagation mode which is greater than the frequency of the ultrasound signals emitted by the transducers.

Thus, the cutoff frequency for a mode (m,n) in an annular space can be written as follows:

$$f_{mn} = \frac{c}{2\pi} \sqrt{\frac{m^2}{a^2} + \frac{n^2 \pi^2}{h^2}}$$

where c is the propagation speed of sound in the gas under consideration, $$a = \sqrt{\tfrac{1}{2}(a_1^2 + a_2^2)}$$

where $a_1$ is the outside radius of the inner tube, $a_2$ is the inside radius of the outer tube, $h=a_2-a_1$, n represents the index of axisymmetrical modes, and m represents the index of asymmetrical modes.

In air, only the axisymmetrical modes (0,0) and (0,1) will propagate in the longitudinal space as defined above.

The respective cutoff frequencies of these modes are as follows:

$$f_{00}=0$$

$$f_{01}=c/2\,h$$

$$f_{02}=c/h$$

By way of example, by choosing the following numerical values for a gas such as air:

$$a_1=3.5 \text{ mm}$$

$$a_2=8 \text{ mm}$$

$$c=340 \text{ m/s}$$

the following cutoff frequencies are obtained for modes (0,1) and (0,2):

$$f_{01}=37.78 \text{ kHz}$$

$$f_{02}=75.55 \text{ kHz}$$

In the chosen example, the frequency of the ultrasound signals emitted by the transducers is 40 kHz and is thus well below the characteristic frequency of propagation mode (0,2) so only modes (0,0) and (0,1) will propagate.

In other applications, where greater head losses can be accommodated, it may be advantageous to allow the plane mode only to propagate in the longitudinal space 32, in which case the greatest radial dimension h of the flow cross-section of said longitudinal space should be chosen so as to impart a cutoff frequency to said section characteristic of the (0,1) propagation mode that is greater than the frequency of the ultrasound signals emitted by the transducers.

FIGS. 5 to 8 show several variant embodiments for the inner duct 28 suitable for use in the first embodiment of the invention as described with reference to FIGS. 1 to 4.

Figure 5:
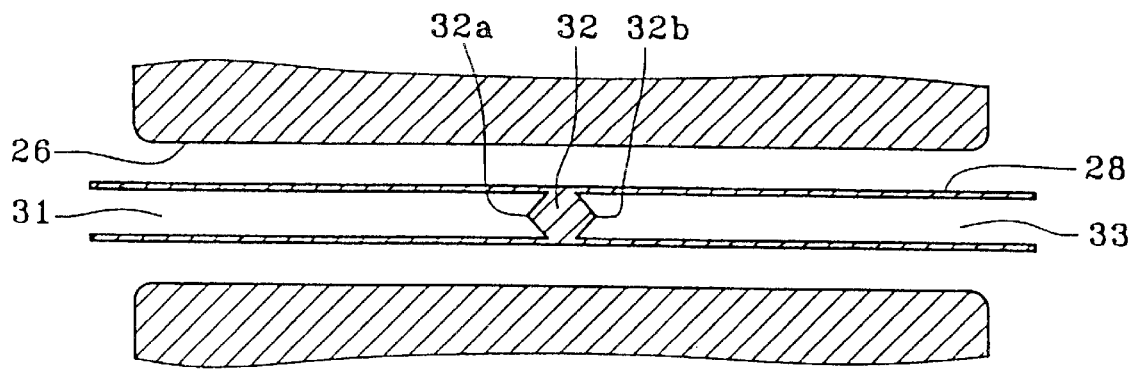
FIGS. 5 to 8 show variant embodiments of the inner duct 28 of the ultrasound measurement device of FIG. 4.

FIG. 5 shows a partition 32 closing the inner duct 28 and presenting respective convex surfaces 32a and 32b (e.g. of conical shape) facing into each of the internal housings 31 and 33. The ultrasound signals emitted by the emitting ultrasound transducer 20 or 24 and propagating along the internal housing 31 or 33 facing the emitting transducer are reflected on the corresponding convex surface 32c or 32d to the inside walls of said internal housing, thereby increasing travel time within the internal housing, and thus increasing the delay before they return to the emitting transducer. As a result the time during which ultrasound signals are emitted can be extended without risk of ultrasound measurements being disturbed, and the same applies to the time during which these signals are received by the other transducer.

Figure 6:
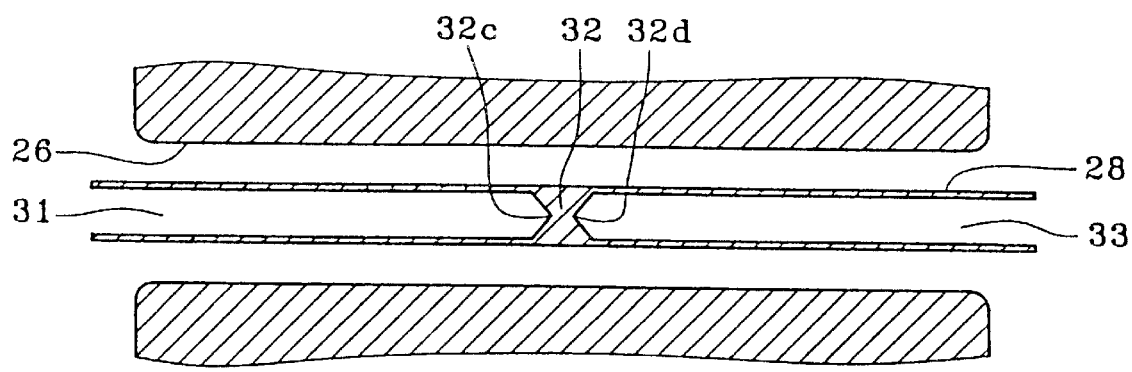

FIG. 6 shows a partition 32 having respective concave surfaces 32c and 32d, e.g. of conical shape, facing each of the internal housings 31 and 33. In a manner analogous to that described above with reference to FIG. 5, the ultrasound signals propagating in the internal housing 31 (or 33 depending on which transducer is emitting) will be subjected to multiple reflections on the inside walls of the corresponding internal housing 31 or 33, thereby delaying the instant at which said signals reach the emitting transducer.

Figure 7:
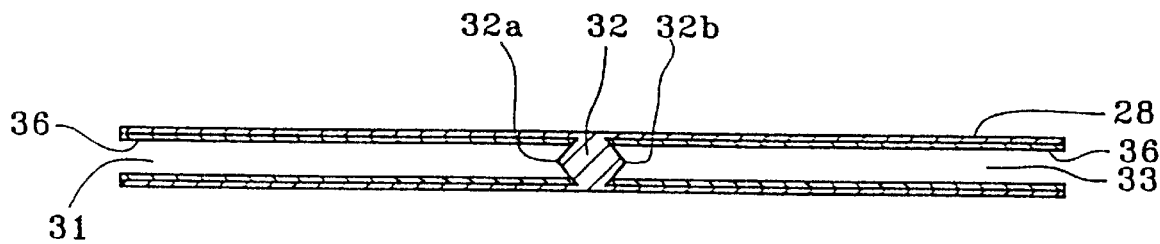
Figure 8:
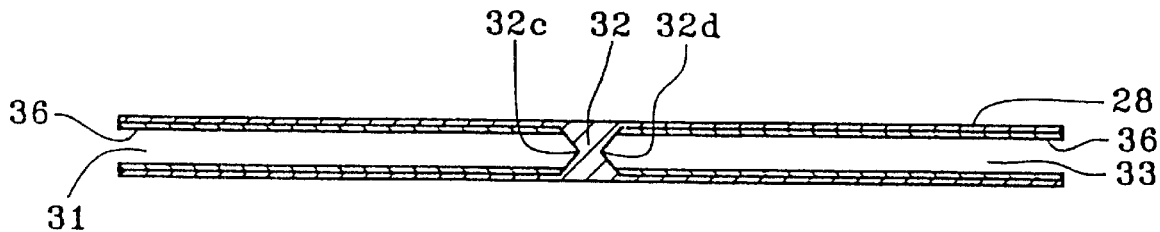

FIGS. 7 and 8 in which only the inner duct 28 is shown relate to a partition 32 obstructing the inner duct, e.g. having a convex surface 32a or 32b facing each of the internal housings 31 or 33 (in FIG. 7) or having a concave surface 32c or 32d (in FIG. 8). Each of the internal housings 31 and 33 is provided over its entire longitudinal dimension or length with a lining 36 made of an ultrasound-absorbent material, thereby making it possible to attenuate or even eliminate the ultrasound signals present in the internal housings after reflection by the convex or concave surfaces 32a, 32b; 32c, 32d. In this way, the ultrasound transducers can continue to emit ultrasound signals without being hindered by interfering signals propagating in the facing internal housing after reflection on the partition 32.

In the embodiment shown in FIGS. 1 to 4, it would also be possible to provide each of the internal housings 31 and 33 with a lining 36 made of an ultrasound-absorbent material so as to attenuate propagation of ultrasound signals in the internal housings.

The element 32 may also include a reflective plane surface so that the ultrasound waves emitted by a transducer 20 or 24 are reflected on said wall and can be detected on return by the transducer. This makes it possible to provide an independent measurement of the speed of the ultrasound wave in the fluid at rest (given that the fluid does not flow inside the tube 28). This measurement makes it possible to take account of variations in the properties of the fluid, such as its density. To perform such a measurement, it should be observed that it is advantageous to increase the length of the path travelled by the wave inside the tube so as to increase the accuracy of the measurement. To do this, the element 32 is located as far as possible from the transducer used for emitting and receiving the wave, e.g. at the end of the tube 28 that is furthest from the transducer. The other face (a non-reflecting face) of the element 32 is then designed to be suitable for diffusing or absorbing ultrasound waves or for reflecting them as in the embodiment shown in FIG. 7.

Figure 9:
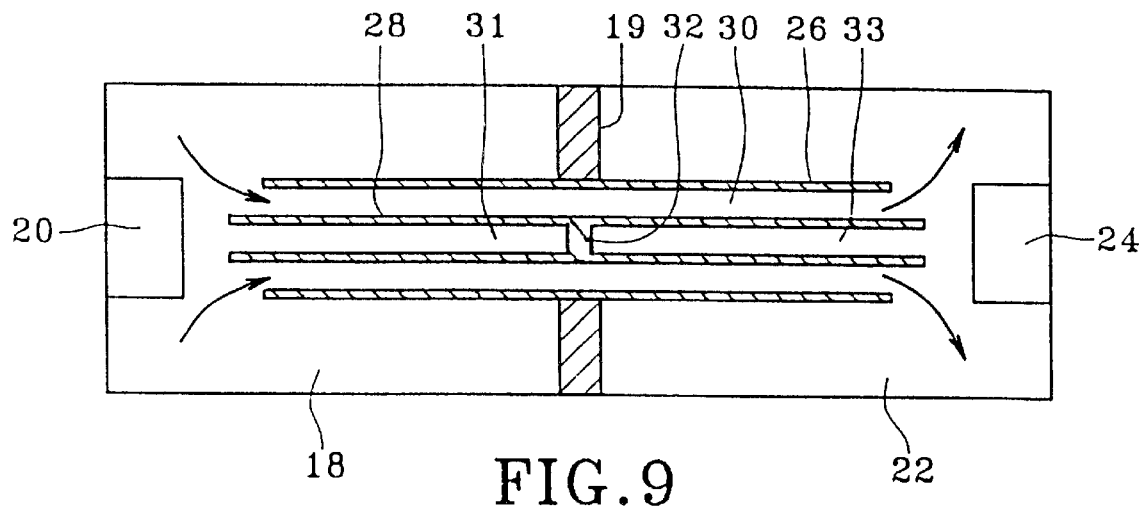
FIG. 9 is a diagrammatic longitudinal section of a second embodiment of the ultrasound measurement device of FIG. 4.

FIG. 9 is a diagrammatic view analogous to FIG. 4 and showing a second embodiment of the measurement device of the invention. In FIG. 9, there can be seen two ultrasound transducers 20 and 24 in alignment on the longitudinal direction XX' and housed respectively in the two measurement chambers 18 and 22, with a wall 19 separating said measurement chambers.

Two tubes that are concentric about the axis XX' pass through the wall 19 and interconnect the measurement chambers 18 and 22 in symmetrical manner about said wall. The configuration of the longitudinal space 20, of the inner and outer ducts 28 and 26, and of the central element 32 is identical to that described with reference to FIGS. 1 to 4.

Figure 10:
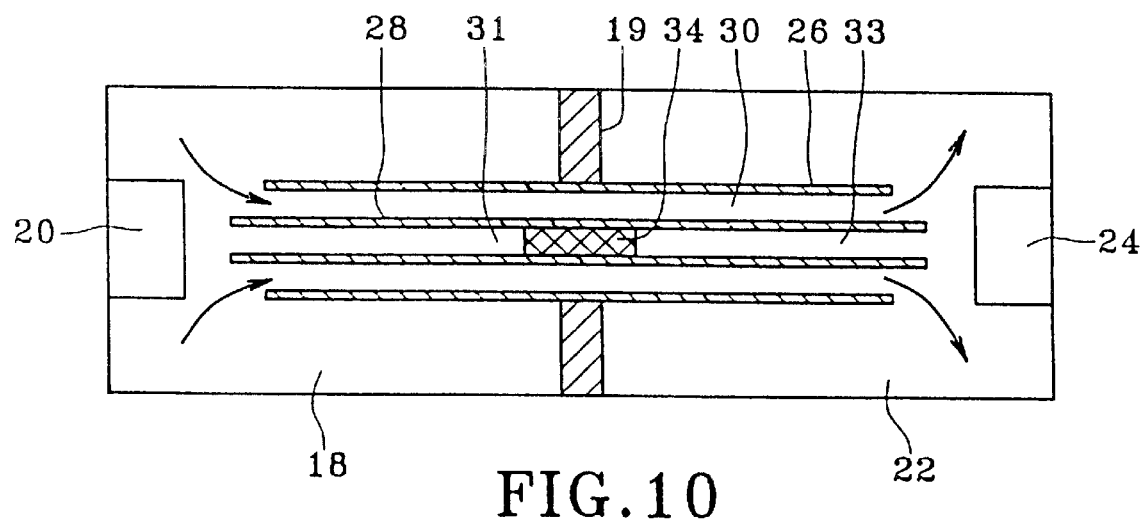
FIGS. 10 to 12 show variant embodiments of the inner duct 28 of the ultrasound measurement device of FIG. 9.

In a variant of the embodiment of the invention shown in FIG. 9, the central element is a filler element 34 made of an ultrasound absorbent material, as can be seen in FIG. 10. Thus, the ultrasound signals propagating within the internal housings are attenuated or even eliminated on reaching the filler element 34 and as a result the risks of ultrasound measurements performed in the longitudinal space 30 being disturbed are considerably reduced.

Figure 11:
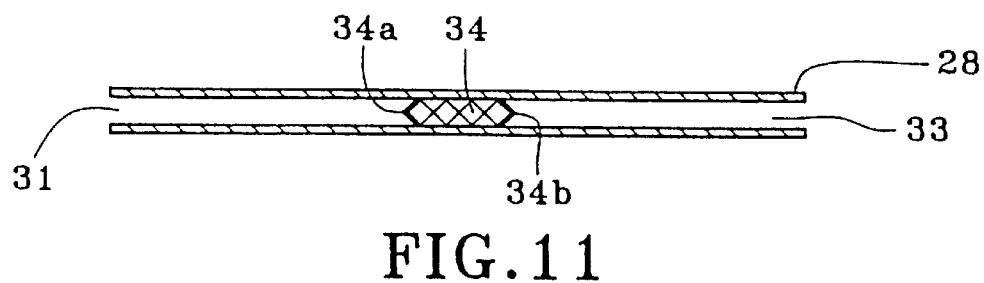
Figure 12:
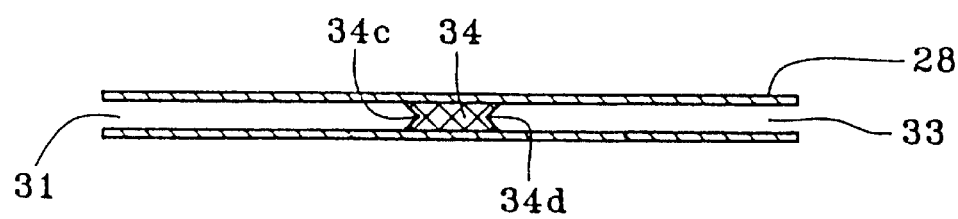

In another variant, as shown in FIG. 11, the filler element 34 made of an ultrasound-absorbent material may also have a convex surface, e.g. a conical surface 34a or 34b looking into each of the internal housings 31 and 33. Likewise, it could have a convex surface, e.g. a conical surface 34c or 34d looking into said housings, as shown in FIG. 12 (in both figures, only the inner duct 28 is shown).

In this way, it is possible to attenuate propagation of ultrasound signals in the internal housings 31 and 33 because they are absorbed by the material constituting the filler element 34 and because of their multiple reflections on the inside walls of the housings 31 and 33 due to the convex or concave shapes of the surfaces of said filler element 34.

It is also possible to line each of the internal housings 31 and 33 with ultrasound-absorbent material so as to trap ultrasound signals propagating in the internal housings completely.

It should be observed that the partition 32 shown in FIGS. 1, 3, and 4 may be replaced by the filler element 34 as described with reference to FIGS. 10 to 12.

To ensure that the device of the invention is effective and restricts the number of propagation modes available in the longitudinal space 30, it is necessary for the inside surface of the outer duct 26 to present no facing portions that are mutually parallel.

Figure 13:
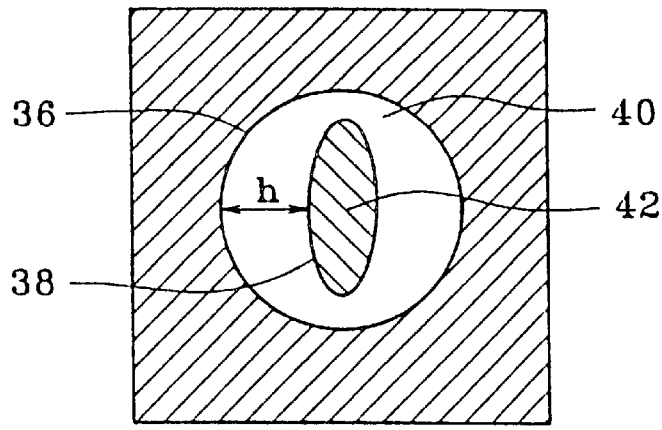
FIG. 13 is a diagrammatic cross-section on a larger scale on BB showing a first variant embodiment of the concentric ducts in the device of FIGS. 1 to 4.

FIG. 13 is a diagrammatic cross-section on BB and on a larger scale showing a variant of the first embodiment of the invention. In this figure, the outer duct 36 is in the form of a tube while the inner duct 38 has a cross-section that is elliptical in shape. The cross-section of the longitudinal space 40 has a greatest radial dimension written h which needs to be dimensioned in such a manner as to filter out certain modes of propagation. As described above for two concentric tubes, it is possible to select this dimension so as to allow plane mode only to appear.

The central portion of the inner duct 38 is obstructed by a partition 42 so as to allow gas to flow and ultrasound measurements to be performed in the longitudinal space 40, only.

Figure 14:
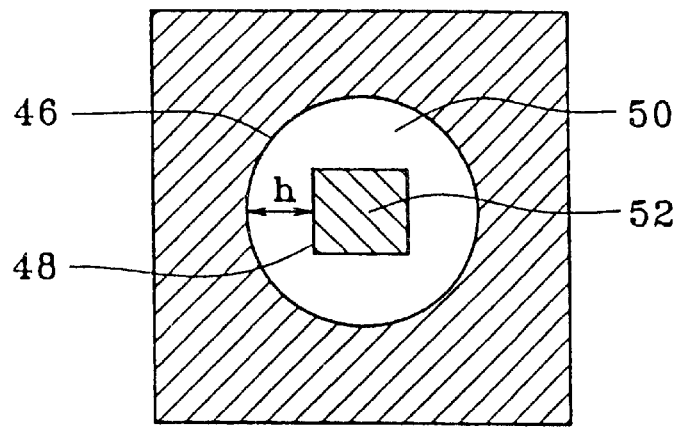
FIG. 14 is a diagrammatic cross-section on a larger scale on BB showing a second variant embodiment of the concentric ducts in the device of FIGS. 1 to 4.

FIG. 14 is a diagrammatic cross-section view on BB and on a larger scale showing another variant of the first embodiment of the invention. In this figure, the outer duct 46 is still in the form of a tube, whereas the inner duct 48 has a cross-section that is square in shape. The cross-section of the longitudinal space 50 has a largest radial dimension that is written h. The central portion of the inner duct 48 is obstructed by a partition 52.

Figure 15:
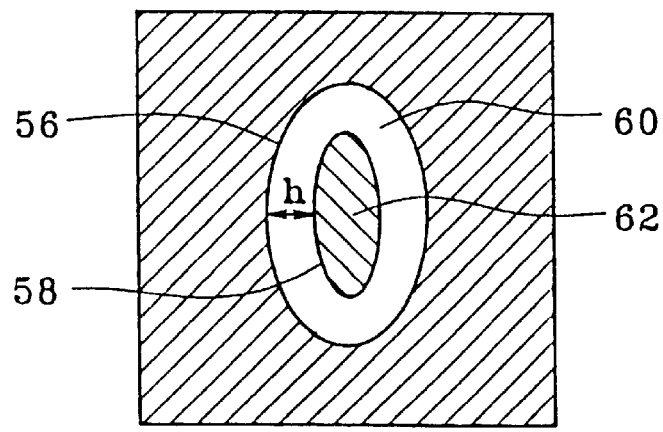
FIG. 15 is a diagrammatic cross-section on a larger scale on BB showing a third variant embodiment of the concentric ducts in the device of FIGS. 1 to 4.

FIG. 15 is a diagrammatic cross-section on BB and on a larger scale showing another variant of the first embodiment of the invention. In this figure, both the outer duct 56 and the inner duct 58 have a cross-section that is elliptical in shape, thereby causing the longitudinal space 60 to be in the form of an elliptical ring. The cross-section of the longitudinal space 62 has a largest radial dimension that is written h. The central portion of the inner duct 58 is obstructed by a partition 62.

Other configurations of the measurement device of the invention may also be envisaged with a different disposition of the ultrasound transducers (they need not necessarily lie on the longitudinal axis XX' of the ducts) by using ducts of other shapes and with a longitudinal space whose cross-section may vary.

Figure 16:
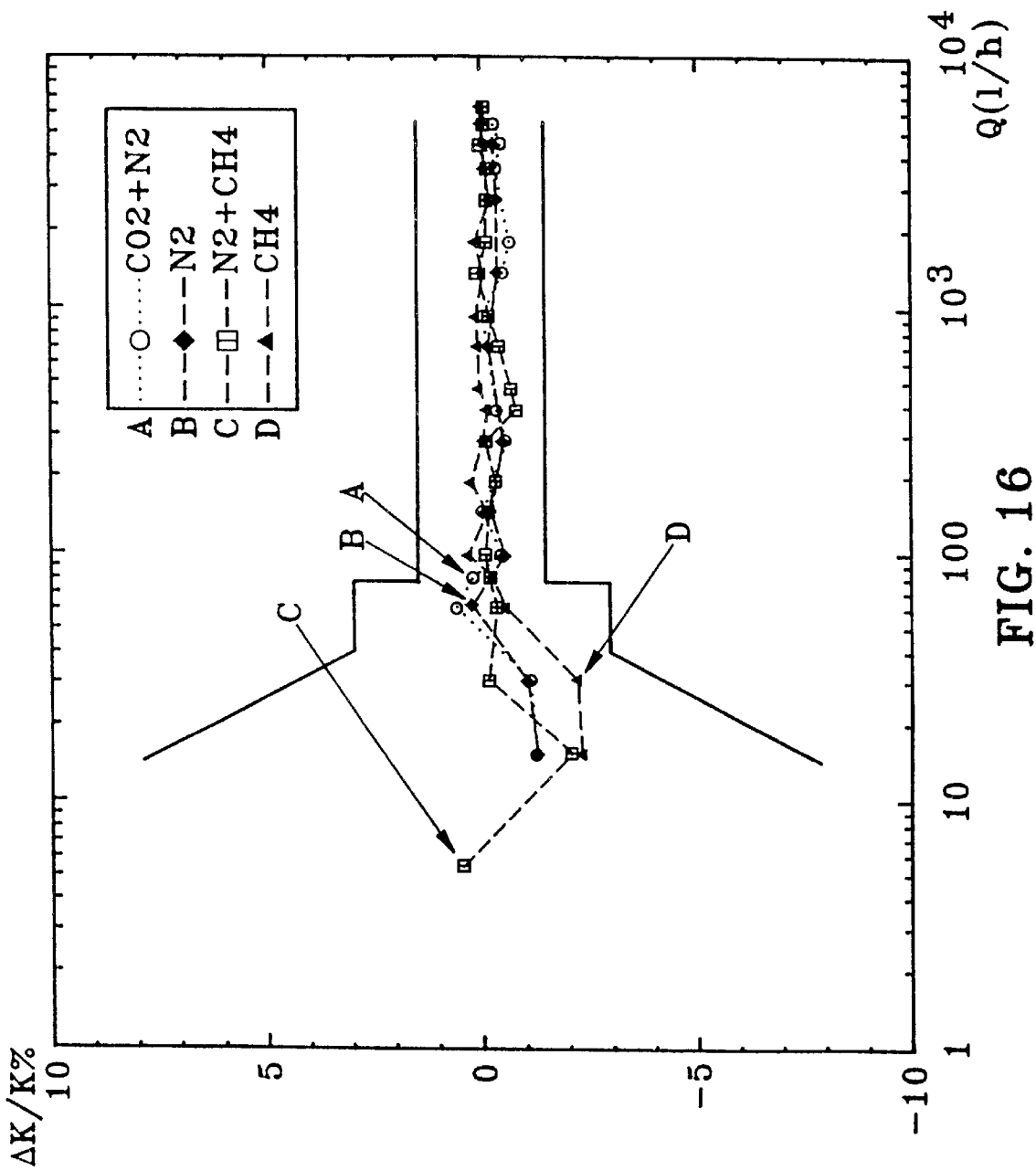
FIG. 16 is a graph showing several calibration curves as obtained using different gases in the ultrasound measurement device of FIG. 10.

FIG. 16 shows various calibration curves obtained for different gases (carbon dioxide and nitrogen: curve A; nitrogen: curve B; nitrogen and methane: curve C; and methane: curve D) using the ultrasound measurement device of the invention as shown in FIG. 10, and for which the greatest radial dimension of the flow cross-section in the longitudinal space 30 gives said flow cross-section a cutoff frequency $f_c$ characteristic of the (0,2) propagation mode which is greater than the frequency of the ultrasound signals emitted by the transducers. The ultrasound transducers 20 and 24 are of the axisymmetrical type, emitting at an ultrasound frequency of 40 kHz, and they are situated at a distance from the corresponding ends 28a and 28b of the inner duct 28 that is equal to 0.5 l where l=0.9 D. The length of the outer duct 26 is 100 mm.

The above-defined radii $a_1$ and $a_2$ are respectively equal to 3.5 mm and to 8 mm. The graph shows relative variation in the factor K (where K is equal to the product of the Reynolds number multiplied by the diameter and divided by the dynamic viscosity) as a function of gas flow rate, and it can be seen that the device of the invention serves firstly to improve the linearity of the calibration curves, and secondly is practically independent of the properties of the particular gas used.

We claim:

1. An ultrasound measurement device for measuring a volume-related quantity of a fluid flowing from a first zone to a second zone of said device, the device including at least two ultrasound transducers suitable for emitting and for receiving ultrasound signals, each being disposed in one of said zones of the device and defining between them an ultrasound measurement path in the fluid, the device also having means for determining the volume-related quantity of said fluid from measurements of at least one physical magnitude characteristic of the propagation speed of the ultrasound signals in the fluid, the ultrasound measurement device being characterized in that said ultrasound measurement device further includes firstly, in at least a portion of the ultrasound measurement path, two concentric ducts about a longitudinal axis, comprising an outer duct having an inner surface and an inner duct having an outer surface, said inner and outer surfaces of said respective outer and inner ducts, defining a longitudinal space therebetween, and secondly, means enabling ultrasound measurement to be performed solely using the receiving signal from the longitudinal space and wherein the inner duct is obstructed by a element subdividing the inside of said inner duct into two internal housings.

2. A device according to claim 1, characterized in that the element is placed in a portion of the inner duct.

3. A device according to claim 1, characterized in that the element has a concave surface facing each of the internal housings.

4. A device according to claim 1, characterized in that the element has a convex surface facing each of the internal housings.

5. A device according to claim 1, characterized in that the element is a partition secured to the inner duct.

6. A device according to claim 1, characterized in that the element is a filler element made out of an ultrasound-absorbent material.

7. A device according to claim 1, characterized in that each internal housing has a longitudinal dimension and is provided over at least a portion of each longitudinal dimension with a lining made of an ultrasound-absorbent material.

8. A device according to claim 1, characterized in that the longitudinal space has a flow cross-section that is constant over an entire longitudinal dimension of said longitudinal space.

9. A device according to claim 1, characterized in that the inner duct has a longitudinal dimension that is greater than the longitudinal dimension of the outer duct and is disposed symmetrically relative to said outer duct.

10. A device according to claim 1, characterized in that the two transducers are in alignment along the longitudinal direction on the axis.

11. A device according to claims 9 and 10, characterized in that each of the outer and inner ducts possesses two respective longitudinal ends facing the transducers and said two respective longitudinal ends being situated at distances l and e from said transducers, where e lies in the range 0.1 l, and 0.9 l, and l lies in the range 0.3 D and 3 D, where D is the inside diameter of the outer duct.

12. A device according to claim 1, characterized in that the longitudinal space has a flow cross-section whose largest radial dimension imparts a cutoff frequency characteristic of (0, 2) propagation mode to said flow cross-section that is greater than the frequency of the ultrasound signals emitted by the transducers.

13. A device according to claim 1, characterized in that the longitudinal space has a flow cross-section whose largest radial dimension imparts a cutoff frequency characteristic of propagation mode to said flow cross-section that is greater than the frequency of the ultrasound signals emitted by the transducers.

14. A device according to claim 1, characterized in that the concentric ducts are tubes, thus conferring a flow cross-section to the longitudinal space which is annular in shape.

15. A device according to claim 1, characterized in that the outer duct is a tube and the inner duct has a cross-section that is elliptical in shape.

16. A device according to claim 1, characterized in that the outer duct is a tube and the inner duct has a cross-section that is square in shape.

17. A device according to claim 1, characterized in that both concentric ducts have a transverse cross-section that is elliptical in shape.

18. A device according to claim 1, characterized in that said element includes a reflecting face enabling the propagation speed of said ultrasound signals in the fluid at rest to be measured.

19. A device according to claim 18, characterized in that the inner duct has two opposite ends, one of which being the farthest from one of the ultrasound transducers so as to measure the propagation speed of ultrasound signals in the fluid at rest, said element being placed in said inner duct at said farthest end.

* * * * *